United States Patent
Nguyen

(10) Patent No.: US 6,616,693 B1
(45) Date of Patent: Sep. 9, 2003

(54) FLEXIBLE FIXATION MEMBERS FOR ANGLE-SUPPORTED ANTERIOR CHAMBER INTRAOCULAR LENSES

(75) Inventor: Robert T. Nguyen, Santa Ana, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

(21) Appl. No.: 09/847,957

(22) Filed: May 3, 2001

Related U.S. Application Data

(60) Provisional application No. 60/201,844, filed on May 3, 2000.

(51) Int. Cl.⁷ .................................................. A61F 2/16
(52) U.S. Cl. ...................................... 623/6.43; 623/6.49
(58) Field of Search ............................... 623/6.43–6.46, 623/6.49, 6.56, 6.38

(56) References Cited

U.S. PATENT DOCUMENTS

| | | |
|---|---|---|
| 4,077,071 A | 3/1978 | Freeman |
| 4,134,160 A | 1/1979 | Bayers |
| 4,174,543 A | 11/1979 | Kelman |
| 4,249,272 A | 2/1981 | Polar |
| 4,254,509 A | 3/1981 | Tennant |
| 4,254,510 A | 3/1981 | Tennant |
| 4,316,293 A | 2/1982 | Bayers |
| 4,370,760 A | 2/1983 | Kelman |
| 4,377,873 A | 3/1983 | Reichart, Jr. |
| 4,403,353 A | 9/1983 | Tennant |
| 4,404,694 A | 9/1983 | Kelman |
| 4,424,597 A | 1/1984 | Schlegel |
| 4,446,581 A | 5/1984 | Blake |
| 4,480,340 A | 11/1984 | Shepard |
| 4,551,864 A | 11/1985 | Akhavi |
| 4,556,998 A | 12/1985 | Siepser |
| 4,560,383 A | 12/1985 | Leiske |
| 4,605,409 A | 8/1986 | Kelman |
| 4,605,411 A | 8/1986 | Fedorov et al. |
| 4,629,460 A | 12/1986 | Dyer |
| 4,629,462 A | 12/1986 | Feaster |
| 4,676,791 A | 6/1987 | LeMaster et al. |
| 4,676,792 A | 6/1987 | Praeger |
| 4,681,102 A | 7/1987 | Bartell |
| 4,687,484 A | 8/1987 | Kaplan |
| 4,687,485 A | 8/1987 | Lim et al. |
| RE32,525 E | 10/1987 | Pannu |
| 4,725,277 A | 2/1988 | Bissonette |

(List continued on next page.)

FOREIGN PATENT DOCUMENTS

| | | |
|---|---|---|
| FR | 2745711 | 9/1997 |
| WO | 98/56315 | 12/1998 |

OTHER PUBLICATIONS

Apple et al., "Anterior chamber lenses. Part 1: Complications and pathology and a review of designs", *J. Cat. Refrac. Surg.*, vol. 13, pp. 157–174, Mar. 1987. (Best available copy).

Marinho, A., "Results are encouraging for phakic IOLs, but more work is needed", *Ocular Surgery News*, Refractive Surgery, pp. 12–15, Feb. 15, 2000.

(List continued on next page.)

*Primary Examiner*—David H. Willse
*Assistant Examiner*—Suzette J. Jackson
(74) *Attorney, Agent, or Firm*—Stout, Uxa, Buyan & Mullins, LLP; Frank Uxa; Peter Jon Gluck

(57) ABSTRACT

An intraocular lens having an optic and a plurality of fixation members coupled to the optic. The fixation members are adapted to flex about points located closer to the outer edge of the IOL than to the optic. The fixation members may have a converging width intermediate region projecting outward from the optic and a pair of leg portions extending generally perpendicularly thereto. The leg portions include foot members and flex radially inward with respect to the intermediate region. Because the optic and intermediate regions are relatively stable, the leg portions flex inward but the optic does not vault or bow upon a compressive fit within the surrounding eye.

20 Claims, 5 Drawing Sheets

U.S. PATENT DOCUMENTS

| | | |
|---|---|---|
| 4,734,095 A | 3/1988 | Seipser |
| 4,781,717 A | 11/1988 | Grendahl |
| 4,787,904 A | 11/1988 | Severin et al. |
| 4,834,748 A | 5/1989 | McDonald |
| 4,863,539 A | 9/1989 | Lee et al. |
| 5,019,097 A | 5/1991 | Knight et al. |
| 5,047,052 A | 9/1991 | Dubroff |
| 5,071,432 A | 12/1991 | Baikoff |
| 5,078,742 A | 1/1992 | Dahan |
| 5,133,749 A | 7/1992 | Nordan |
| 5,147,395 A | 9/1992 | Willis |
| 5,147,397 A | 9/1992 | Christ et al. |
| 5,197,981 A | 3/1993 | Southard |
| 5,201,763 A | 4/1993 | Brady et al. |
| 5,203,790 A | 4/1993 | McDonald |
| 5,225,858 A | 7/1993 | Portney |
| 5,258,025 A | 11/1993 | Fedorov et al. |
| 5,433,745 A | 7/1995 | Graham et al. |
| 5,476,513 A | 12/1995 | Brady et al. |
| 5,628,796 A | 5/1997 | Suzuki |
| 5,716,403 A | 2/1998 | Tran et al. |
| 5,928,282 A * | 7/1999 | Nigam ............ 623/6.43 |
| 6,015,435 A | 1/2000 | Valunin et al. |
| 6,051,024 A | 4/2000 | Cumming |
| 6,152,958 A * | 11/2000 | Nordan ............ 523/6.25 |
| 6,179,870 B1 | 1/2001 | Sourdille et al. |
| 6,200,344 B1 * | 3/2001 | Lamiellee et al. ...... 623/6.51 |
| 6,224,628 B1 * | 5/2001 | Callahan et al. ........ 623/6.4 |
| 6,261,321 B1 | 7/2001 | Kellan |

OTHER PUBLICATIONS

Baikoff et al., "Angle–fixated Anterior Chamber Phakic Intraocular Lens for Myopia of −7 to −19 Diopters", *J. Refrac. Surg.*, vol. 14, pp. 282–293, May/Jun. 1998.

Alió et al., "Phakic Anterior Chamber Lenses for the Correction of Myopia", *Ophthalmology*, vol. 106, No. 3, pp. 458–466, Mar. 1999.

Apple et al., "Intraocular Lenses—Evolution, Designs, Complications, and Pathology", pp. 23–36 and pp. 205–221, Williams & Wilkins Copyright ® 1989.

CILCO advertisement brochure, Oct. 1982, 3 pages.

Praeger, Copeland Lens, 1982, 7 pages.

* cited by examiner

FLEXIBLE FIXATION MEMBERS FOR ANGLE-SUPPORTED ANTERIOR CHAMBER INTRAOCULAR LENSES

RELATED APPLICATION

This application claims the benefit of U.S. provisional application Serial No. 60/201,844, filed May 3, 2000, the disclosure of which is incorporated in its entirety herein by reference.

BACKGROUND OF THE INVENTION

This invention relates to intraocular lenses (IOLs) More particularly, the invention relates to IOLs placed in the anterior chambers of eyes which provide at least one of the following benefits: a reduction in the incidence of one or more complications in the eye caused by prior anterior chamber IOLs, effective foldability for safe and controlled insertion in the eye through a small incision, reduced IOL retention forces and a reduction in the tendency of the optics of the IOLs to vault due to a desirable compressive bias of the IOL when fit within the eye.

Intraocular lenses (IOLs) are commonly used to modify or enhance vision. IOLs can be placed at various positions or locations within the eye. For example, IOLs can be placed in the anterior chamber (AC) of the eye, that is, the region of the eye posterior of the cornea and anterior of the iris.

IOLs may generally be classed by material. Hard or rigid IOLs are distinguished from soft IOLs that may be folded to facilitate implantation through a small incision in the cornea (and capsular bag for posterior lenses).

Although there are substantial advantages to placing the IOL in the anterior chamber of the eye, various complications have been reported as a result of the presence of IOLs in such anterior chambers. For example, anterior chamber IOLs have been reported to cause detrimental endothelial cell loss in the eye; pupil retraction or ovalling, which can be both cosmetically and functionally detrimental; pupillary block, which can cause glaucoma; and decentration or offsetting displacement of the IOL away from a preferred optical axis. Such complications are particularly troublesome when the anterior chamber IOL is structured to be fixated against the iridio/corneal angle, a very delicate region of the eye. It would be advantageous to provide anterior chamber IOLs which result in reduced incidences of one or more of these complications.

IOLs advantageously have been foldable for insertion through small incisions in eyes, particularly for insertion in the capsular bags in the posterior chambers of the eyes. Because of space constraints in and the delicacy of the anterior chamber, IOLs for insertion in the anterior chamber are not generally foldable. For example, IOLs have a tendency to move in a relatively uncontrolled manner upon unfolding in the eye. Such uncontrolled movement of an IOL in the anterior chamber can detrimentally affect the iris and/or the cornea. For example, the IOL touching the cornea can result in harmful endothelial cell loss.

When implanted, both soft and rigid anterior chamber IOLs exert retention forces on their outer ends; that is, the IOL is typically slightly oversized relative to the peripheral anterior chamber structure. A slight amount of such retention forces is desirable so that the lens is held in place or centered, otherwise a loose fit might cause vision and other problems. Indeed, some earlier rigid IOLs were unsatisfactory because of sizing difficulties, in that the size of the IOL relative to the surrounding tissue was critical. On the other hand, both "rigid" and "soft" IOLs may be provided with some flexibility in the plane of the IOL to mitigate against such sizing concerns. The term "plane" or "surface" of the IOL will be used to denote the surface (and extension thereof) of the optic portion of the IOL, though it will be understood that such a "plane" may actually be a partial sphere or other curved surface.

As stated, anterior chamber IOLs may be oversized and flexible in the plane of the IOL such that they are placed in compression when implanted. However, a balance must be observed between sufficient compression for a good fit and unwanted endothelial cell loss and pupil ovalling from excessive compression. In addition, the design of the footplates must be such that over time, pupil block and glaucoma does not result. Finally, the problems of corneal touch and further endothelial cell loss may arise in some current IOLs, whether formed of soft or rigid materials, which may deflect along the optical axis even with only a small magnitude of compressive fit. As a result, IOL manufacturers must provide a range of sizes to fit the IOL to a particular patient's eye and reduce, or even substantially minimize, retention forces and the potential for axial deflection.

U.S. Pat. No. 5,928,282 discloses an intraocular lens having haptics that are flexible to minimize translational motion of the optic along the optical axis. The patent discloses a central portion (38) extending between a foot plate on the outer end of the haptic and the IOL optic that has a thickness dimension (parallel to the optical axis) equal to or greater than a width dimension. A transition portion (44) extends from the central portion to the foot plate and has a gradually decreasing thickness and increasing width, with the foot plate being relatively flat. In this design, the central portion is flexible to mitigate against the perceived problem of inward compression of the surrounding eye without undue axial movement, or doming, of the optic. Unfortunately, the central portions extend to within proximity of the optic, and their flexibility thus creates the potential for unwanted optic movement. That is, the dynamic system of the IOL consists of the optic supported within a number of relatively flexible haptics.

It would be advantageous to provide soft anterior chamber IOLs which provide one or more of the following: reduced incidences of one or more known complications caused by prior anterior chamber IOLs, are effectively and safely foldable for insertion in the eye, safely and effectively fit a range of sizes of eyes, provide reduced retention forces, minimize translational movement of the optic of the IOL along the optical axis from the compressive fit in the eye, and which otherwise stabilize the optic from unwanted movement.

SUMMARY OF THE INVENTION

New IOLs for implantation in eyes, in particular in anterior chambers of the eyes, have been discovered. The present IOLs are sized and structured to reduce the incidence of one or more known complications in the eye caused by prior anterior chamber IOLs. The present IOLs are designed to be effectively fixated against the iridio/corneal angle of the anterior chamber while being substantially compatible with this delicate region of the eye. Reduced endothelial cell loss and/or reduced pupil ovalling and/or reduced pupilliary block, for example, relative to prior anterior chamber IOLs, are obtained in accordance with the present invention.

The present IOLs are foldable for insertion through a small incision in the eye. In particular, the IOLs of the present invention are designed and structured to be folded and inserted, for example, using a forceps or a conventional system used to fold and insert folded IOLs in eyes, effectively and safely. The present IOLs preferably are structured to unfold in the eye in a substantially controlled manner which advantageously reduces the risk of the unfolding IOL causing damage to the eye.

In the eye, the IOL is effectively fixated against the iridio/corneal angle. In this position, the IOL is advantageously stabilized, exerts reduced retention forces, and the optic of the IOL has a substantially reduced tendency to vault anteriorly.

In one embodiment, the present invention provides a foldable intraocular lens (IOL) for implantation in the anterior chamber of an eye. The IOL includes an optic centered on an optical axis, the IOL defining a planar or domed surface that is substantially perpendicular with respect to the optical axis at least at its intersection with the optical axis. At least one fixation member having a proximal end is secured to the optic. An intermediate region extends generally radially outwardly from the proximal end, and a distal region secures to an outer portion of the intermediate region. The distal region includes at least one leg portion extending away from the outer portion of the intermediate region generally perpendicularly with respect to a radial line (relative to the optical axis) through the intermediate region. The leg portion is able to flex in a direction parallel to the planar or domed surface of the IOL while the intermediate region is substantially unable to flex in a direction parallel to the planar or domed surface of the IOL.

In a preferred embodiment, the IOL includes only two of the fixation members. The distal region may have two leg portions extending away from each other in substantially opposite directions, and the two leg portions may extend away from each other a distance equal to or less than a diameter of the optic to facilitate folding of the IOL. Desirably, the leg portions each have an enlarged footplate on an outer end extending radially outwardly therefrom. When implanted, the leg portions are each structured to flex in response to a radially-inwardly directed biasing force being applied to the respective footplate secured thereto. More generally, the leg portion is structured to flex substantially without moving the optic parallel to the optical axis.

In accordance with one aspect of the invention, the intermediate region has a circumferential width about the optical axis which is substantially smaller adjacent the outer portion than it is adjacent the proximal end. Preferably, the intermediate region has a circumferential width that is at least twice as large as its axial thickness at all points. The IOL may be a single piece lens, or the optic and the fixation members may comprise one or more polymeric materials. In a preferred embodiment, the optic comprises a resiliently deformable polymeric material. In one form, the fixation member exhibits an angular transition so as to be stepped from the plane of the IOL.

In accordance with another aspect of the invention, a foldable intraocular lens (IOL) having reduced optic vaulting for implantation in the anterior chamber of an eye is provided. The IOL includes an optic centered on an optical axis, the IOL defining a planar or domed surface that is substantially perpendicular with respect to the optical axis at least at its intersection with the optical axis. At least one fixation member having a proximal end is secured to the optic. An intermediate region extends generally radially outwardly from the proximal end and a distal region secures to an outer portion of the intermediate region. The distal region is able to flex in a direction parallel to the planar or domed surface of the IOL. The intermediate region has a circumferential width about the optical axis which is substantially smaller adjacent the outer portion than it is adjacent the proximal end. Preferably, the intermediate region has a circumferential width that is at least twice as large as its axial thickness at all points. More preferably, the intermediate region has a diverging circumferential width from the outer portion to the proximal end thereof.

Any and all of the features described herein and combinations of such features are included within the scope of the present invention provided that the features of any such combination are not mutually inconsistent.

These and other aspects and advantages of the present invention will become apparent in the following detailed description and claims, particularly when considered in conjunction with the accompanying drawings in which like parts bear like reference numerals.

DESCRIPTION OF THE PREFERRED EMBODIMENTS

Figure 1:
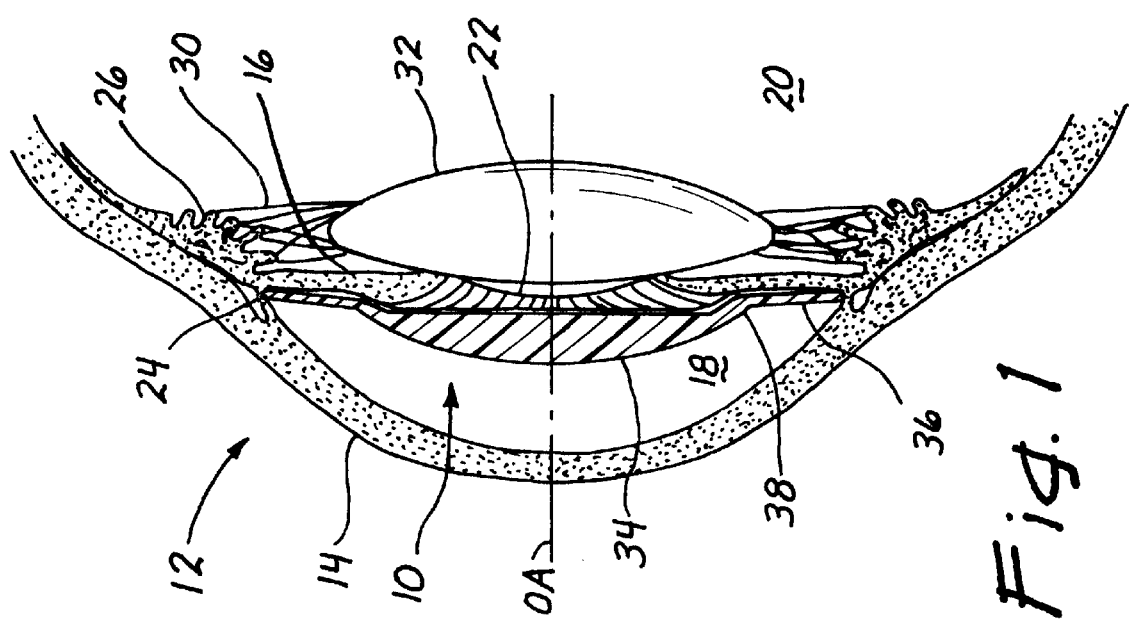
FIG. 1 is a cross-sectional view through a sagittal portion of a human eye, illustrating an IOL of the present invention mounted in the anterior chamber.

Referring now to FIG. 1, an anterior IOL (AIOL) 10 of the present invention is shown implanted in an eye 12. The eye 12 comprises a cornea 14 shown to the left or front of the eye and an annular iris 16 shown in the middle of the eye. The iris 16 divides the eye 12 into an anterior chamber 18 at the front of the eye and a posterior chamber 20 in back of the iris. The iris 16 also defines the aperture or pupil 22, which is a variable opening in the middle of the iris. The posterior face of the cornea 14 and the anterior face of the iris 16 meet at the scleral spur defining an iridio-corneal angle 24. Behind the iris 16 is the ciliary process 26, which controls the movements of the natural crystalline lens 32 of the eye 12 via a plurality of fibrous zonules 30.

FIG. 1 shows a vaulted AIOL 10 of the present invention implanted in the anterior chamber 18 of the eye 12. The AIOL 10 comprises an optic 34 that is supported in front of the pupil 22 by fixation members 36, sometimes known as haptics. The fixation members 36 exhibit an angular transition 38 that steps the optic 34 forward. That is, the optic 34 defines a planar or domed surface perpendicular to the optical axis at least at the intersection with the optical axis, and the angular transition 38 offsets the fixation members 36 from the surface. Desirably, however, the fixation members 36 are located in a common planar or domed surface that is perpendicular to the surface defined by the optic. The fixation members 36 extend radially outward from the typically circular optic 34 to rest in the iridio-corneal angle 24, and, as will be explained below, are designed to minimize retention forces and inhibit forward vaulting of the optic along the optical axis OA.

The optic 34, for the AIOL 10 and other IOLs described herein, may be considered as including an optical portion centered along an optical axis OA for focusing light at or near the retina (not shown) of the eye 12. The optical axis OA is an imaginary line that passes through the optical centers of both surfaces of the AIOL 10, and in the human eye is generally aligned along the centers of the cornea 14, the natural lens 32 and the retina (not shown) of the eye 12. Desirably, the optical axis OA of the AIOL 10 coincides with that of the natural eye.

Figure 2:
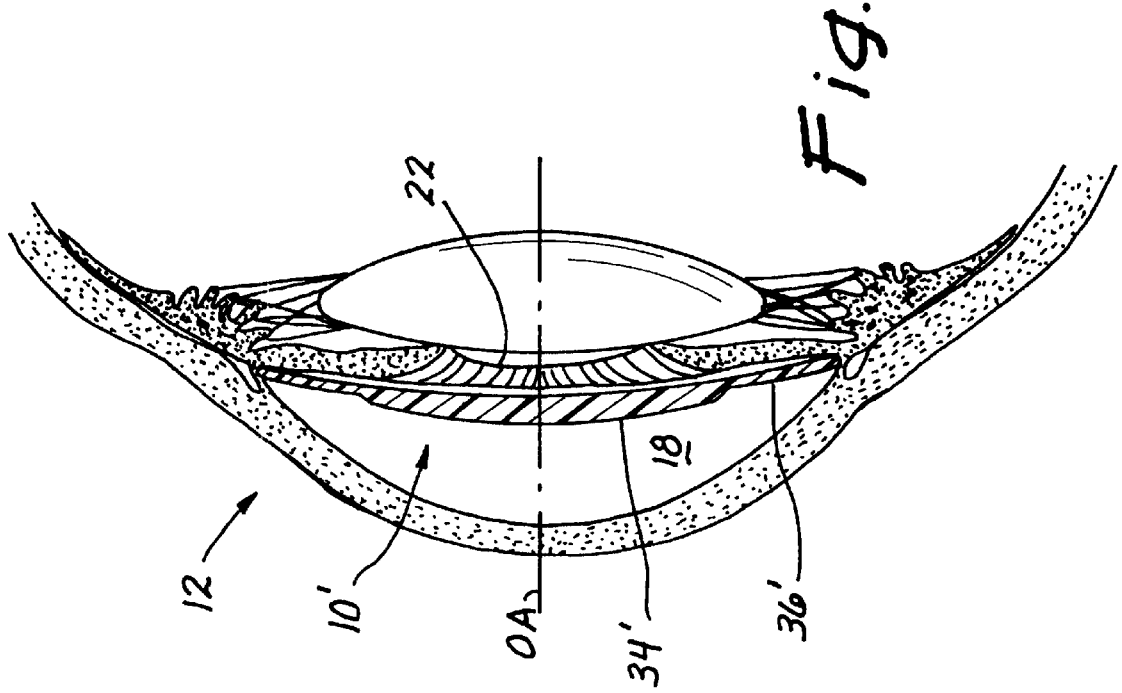
FIG. 2 is a cross-sectional view through a sagittal portion of a human eye illustrating another IOL of the present invention mounted in the anterior chamber.

FIG. 2 shows a non-vaulted AIOL 10' of the present invention implanted in the anterior chamber 18 of the eye 12. The AIOL 10' also comprises an optic 34' that is supported in front of the pupil 22 by fixation members 36'. In contrast to the AIOL 10 of FIG. 1, the fixation members 36' of the non-vaulted AIOL 10' are generally in the same plane (or spherical surface) as the optic 34', without a stepped or angular transition.

Figure 3:
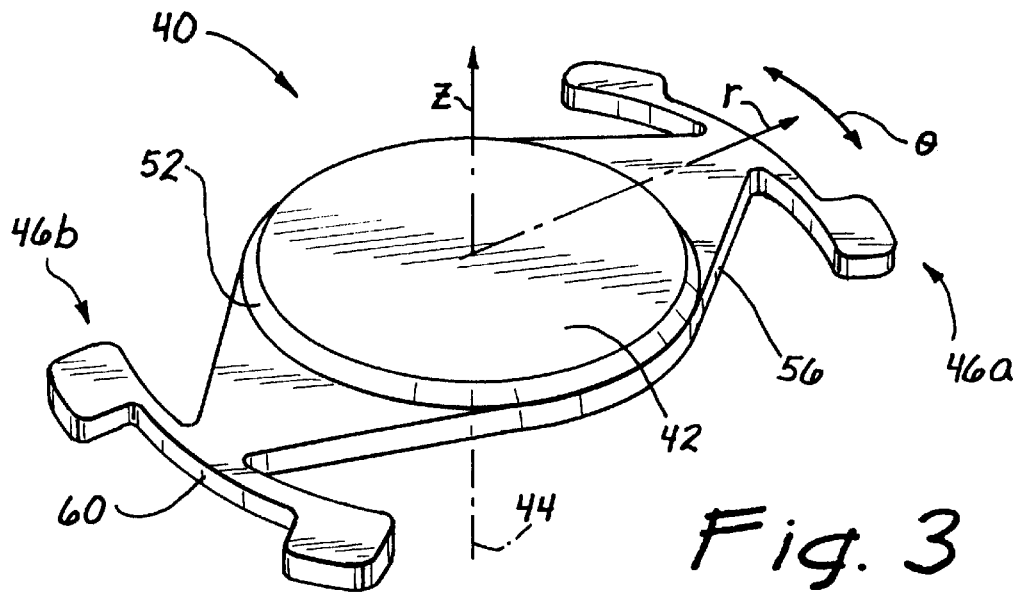
FIG. 3 is a perspective view of an anterior chamber IOL of the present invention, showing reference axes.
Figure 4:
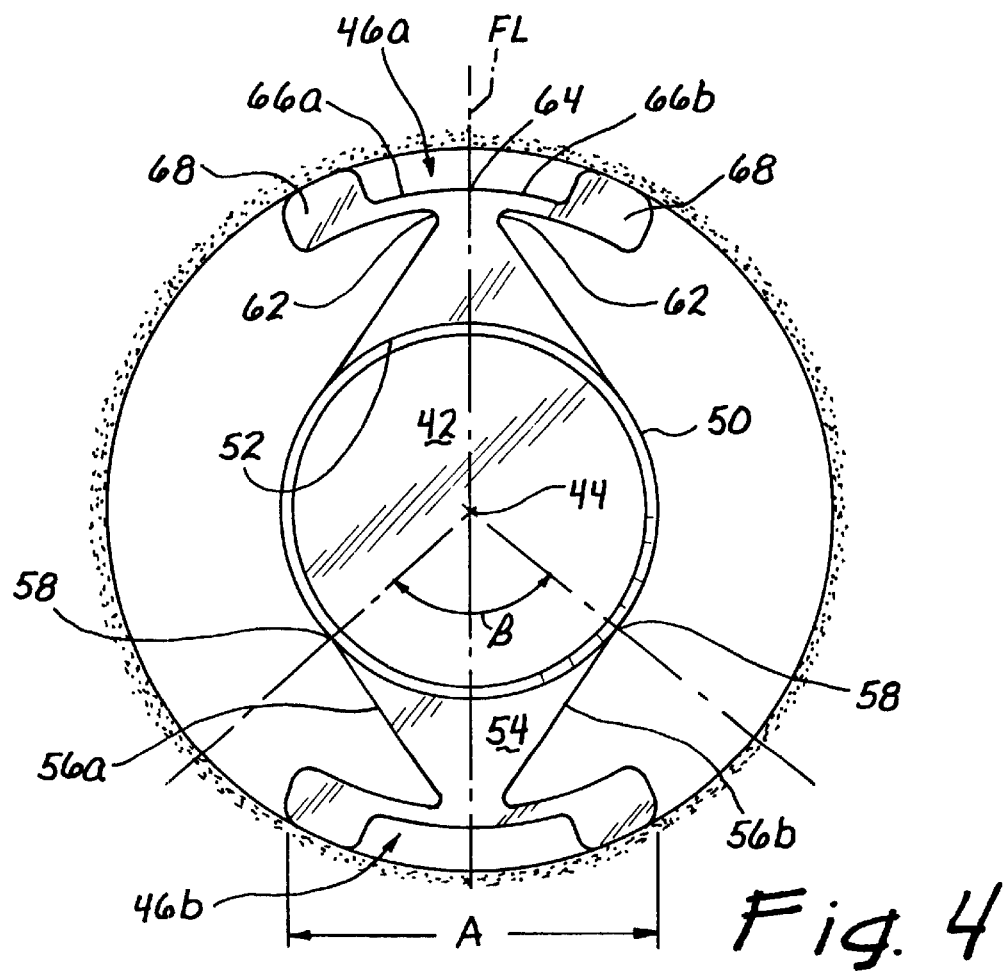
FIG. 4 is a frontal elevational view of the anterior chamber of the eye showing the IOL of FIG. 3 installed therein.

FIGS. 3 and 4 illustrate an exemplary intraocular lens (IOL) 40 of the present invention comprising a generally circular optic 42 defining an optical axis 44, and a pair of fixation members 46a and 46b extending radially outward from the optic at diametrically opposed positions. Reference coordinates are shown, with a Z-axis coinciding with the optical axis 44, a radial direction r extending perpendicularly to the Z-axis, and a circumferential direction Θ in the plane of the IOL and centered about the Z-axis. The IOL 40 is seen in the section (FIGS. 1 and 2) and elevational views (FIG. 4) installed in the anterior chamber of a human eye.

When used as a refractive lens, the optic portion can be a positive powered lens from 0 to approximately +20 diopters, or a negative powered lens from 0 to approximately −25 diopters. The optic portion can be biconvex, plano-convex, plano-concave, biconcave or concave-convex (meniscus), depending upon the power required to achieve the appropriate central and peripheral thickness for efficient handling. In addition, the optic may be single or multi-focal.

The IOLs of the present invention can be made from a variety of so-called soft biocompatible materials that can be folded or compressed, such as silicone polymeric materials, acrylic polymeric materials, hydrogels, hydrogel-forming polymeric materials and mixtures thereof. The fixation members 46 may be formed separately from the optic 42 and connected through processes such as heat or physical staking and chemical bonding, or may be formed as an integral part of the optic 42 in a so-called single-piece IOL. In a preferred embodiment, an IOL of the present invention is made of a material that can be folded for insertion through a small incision (e.g., less than 3.5 mm), and is desirably of one-piece construction.

As best seen in FIG. 4, each fixation member 46 is attached to or formed integrally with a peripheral, preferably circular outer edge 50 of the optic 42. In this regard, each fixation member 46 has a concave proximal end 52 defining the beginning of an outwardly projecting intermediate region 54. The circumferential width (in the Θ direction) of the fixation members 46 at the proximal end 52 is relatively large such that opposite side edges 56a, 56b of the intermediate region 54 terminate at points 58 on the optic outer edge 50 that are spaced apart by an included angle beta. The side edges 56a, 56b desirably converge in a radially outward direction such that they are tangent to the circular outer edge 50 at the points 58.

The side edges 56a, 56b converge and join with a distal region 60 of the fixation member 46 at respective fillets 62. Each distal region 60 comprises a bridge portion 64, a pair of leg portions 66a, 66b extending generally circumferentially away from the bridge portion in opposite directions, and a foot plate 68 provided on the distal end of each of the leg portions. By "generally circumferentially away from the bridge portion" it should be understood that the leg portions 66a, 66b are desirably arcuate and centered about the Z-axis, but may also be straight and extend tangentially from the bridge portion 64. As seen in FIG. 4, therefore, each fixation member 46 generally has a shape of a stylized letter "T".

As mentioned above, the IOL 40 is desirably foldable for insertion through a small incision. With reference to FIG. 4, a fold line FL has been drawn generally indicating the axis about which the IOL 40 is folded. The IOL 40 is folded longitudinally about fold lines parallel to the axis along which the fixation members 46a, 46b extend. To facilitate folding, the leg portions 66a, 66b extend away from each other a distance A that is equal to or less than the diameter of the optic 42. That is, none of the leg portions 66 extend away from the fold line FL a distance greater than the optic 42. In this way, the folded IOL 40 is more compact, without projecting leg portions.

With reference now to FIGS. 5–8, an exemplary structure for each fixation member 46 will be described. The IOL of the present invention is radially flexible such that the fixation members 46 move toward the optic 42 when the IOL is compressively fit in the peripheral ciliary band, with the optic undergoing minimal translational movement along the optical axis OA for preventing decentering of the IOL, distortion of vision, and corneal endothelial touch. This flexibility also permits one or several standard lens sizes of each style to be suitable for eyes of most sizes. By providing universal lenses of this type, the risk of implanting an improper sized lens is reduced.

To accomplish the aforementioned radial flexibility while limiting axial movement of the optic, each fixation member 46 preferably flexes about at least one point located closer to the distal region 60 than to the proximal end 52. At the same time, rotational and torsional stability is provided by an enlarged intermediate region 54. In this manner, dynamic stability is provided to the optic 42 and intermediate region 54, while the distal region 60 flexes.

Figure 8:
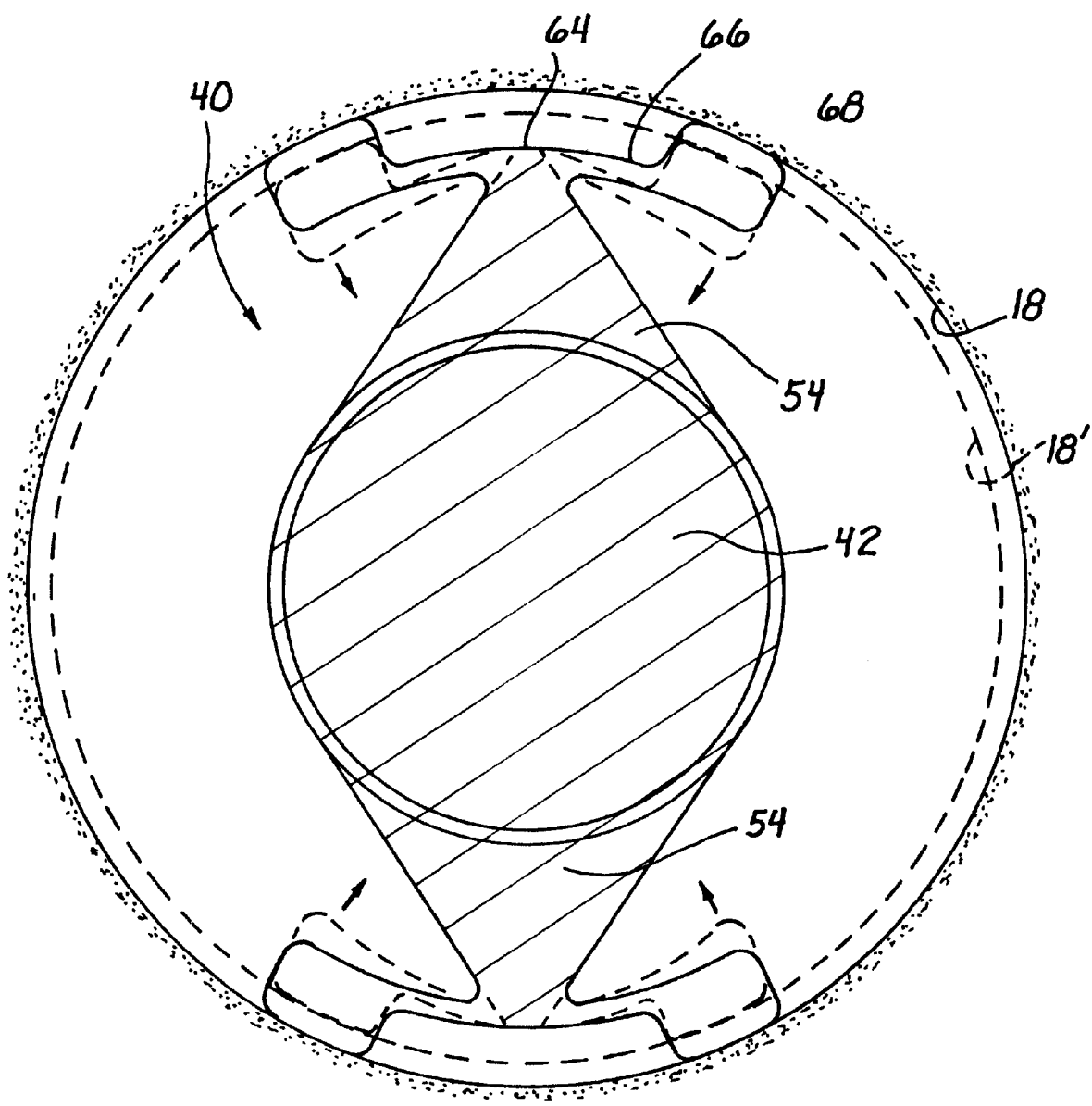
FIG. 8 is a frontal elevational view of the anterior chamber of the eye and the IOL of the present invention installed therein, illustrating preferred flexing of the IOL.

FIG. 8 illustrates, in solid line, the IOL 40 as it would appear in a relaxed state within an identically-sized anterior chamber 18. Although the IOL 40 fits closely within this chamber 18, there is no compression and thus the IOL may tend to slide or otherwise move from its central position.

An actual size anterior chamber 18 is shown in dashed line 18' such that the IOL 40 compresses inward to accommodate the reduced space. Specifically, the anterior chamber 18' acts against each of the foot members 68 to flex the leg portions 66 inward at the fillets 62 and with respect to the bridge portion 64. The flex positions of the leg portions 66 are shown in dashed line. It will be noted that the intermediate region 54 and bridge portion 64 remain relatively unaffected by this compression. Indeed, the cross-hatching superimposed on the IOL 40 indicates that area of the IOL that remains stable and relatively unaffected by the compression imparted by the surrounding eye. The cross-hatched area includes the optic 42, both intermediate regions 54, and a central triangular area in each bridge portion 64. As a result, the optic 42 undergoes little radial compression, and thus remains substantially in place along the optical axis.

There are two main contributing factors to the combination of radial flexibility of the IOL overall, but largely stable inner regions. First, the location of the flexing in each fixation member 46 is closer to the distal region 60 than to the proximal end 52. Secondly, the structure of the intermediate regions 54 is such that the fixation members 46 are relatively inflexible in the plane of the IOL (i.e., the planar or shallow domed surface defined by the IOL), and in torsion about a radial axis therethrough. These features will be expounded upon below.

As stated, the fixation members 46 of the present invention are specifically designed to flex in locations radially closer to the distal regions 60 than to the proximal end 52. Accordingly, each of the leg portions 66 flexes about the bridge portion 64. In their construction, the leg portions 66 are essentially cantilevered about the bridge portion 64 and undergo bending along their entire length out to the foot members 68. Because of this arrangement, the highest bending stresses in the leg portions 66 are located adjacent to the fillets 62.

Figure 5:
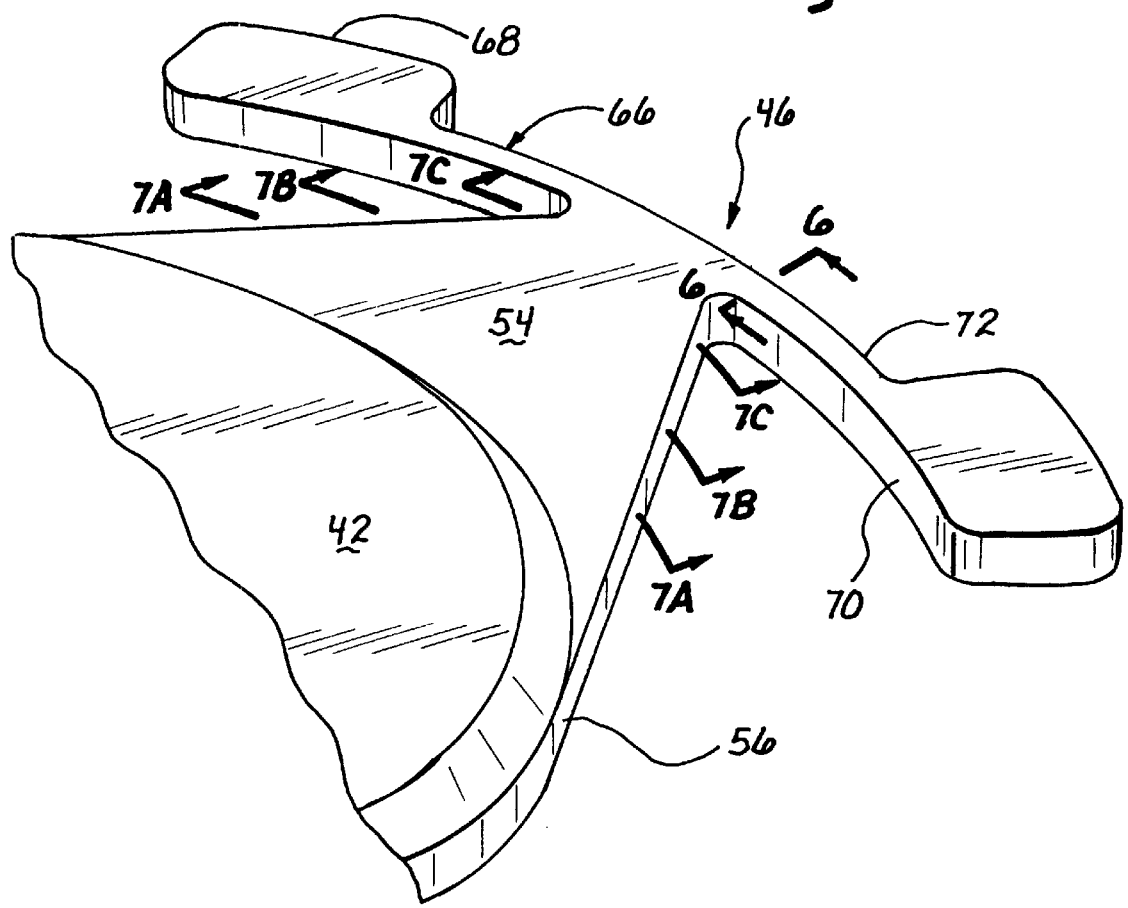
FIG. 5 is an enlarged perspective view of a portion of the IOL of FIG. 3 illustrating an exemplary fixation member.
Figure 6:
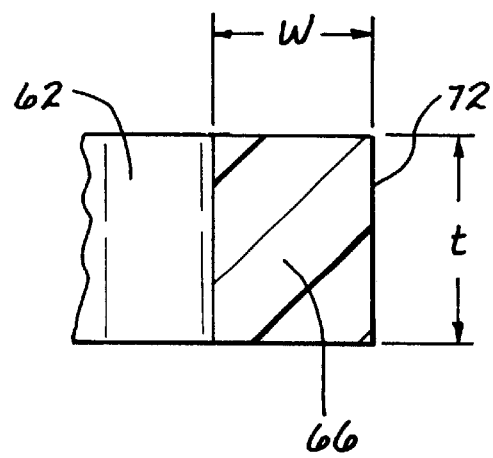
FIG. 6 is a cross-sectional view through a distal region of the fixation member shown in FIG. 5.

FIG. 6 is a cross-section taken along line 6—6 of FIG. 5 through a mid-portion of one of the fillets 62, and shows the relative radial width w and axial thickness t. In a preferred embodiment, the thickness t is greater than the radial width w so that the leg portion 66 is relatively easy to bend about an axis parallel to the Z-axis.

Figure 7A:
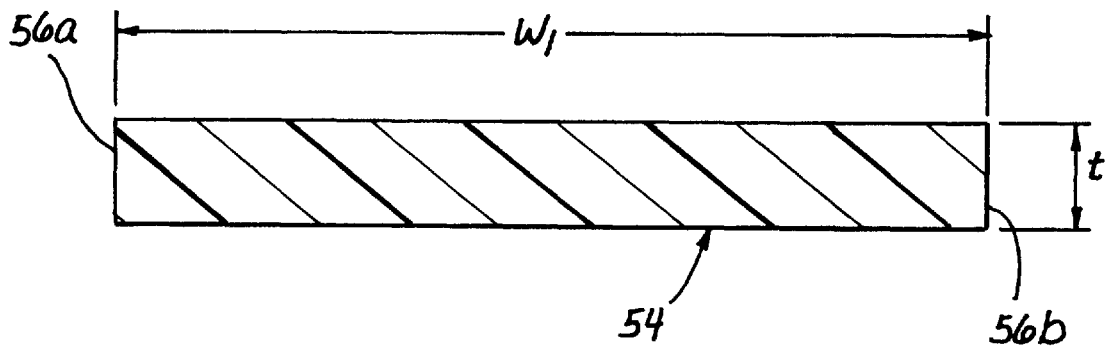
FIGS. 7A–7C are cross-sectional views through an intermediate region of the fixation member taken along corresponding lines in FIG. 5.
Figure 7B:
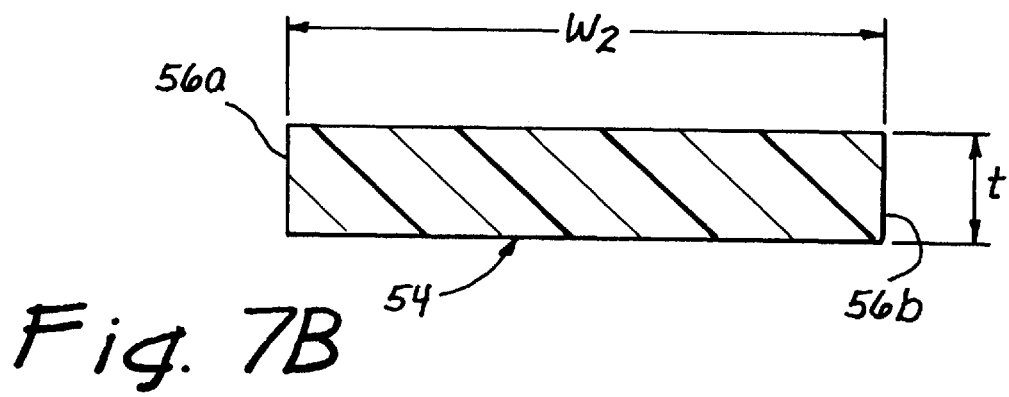
Figure 7C:
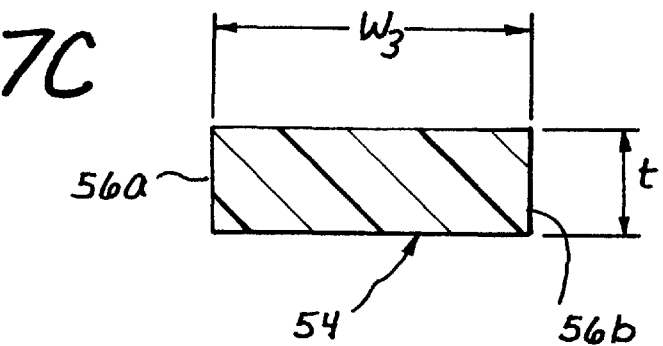

At the same time, the intermediate region 54 is relatively wider in the circumferential direction a than it is thick, and thus resists flexing upon the compression translated through the bridge portion 64 from the leg portions 66. More specifically, FIGS. 7A–7C illustrate several sections of the intermediate region 54 as it progresses radially outward. In a preferred embodiment, the thickness t remained substantially constant throughout the fixation members 46, and at least within the intermediate region 54. In one specific embodiment, t is between about 200–250 μm. The circumferential width w across the intermediate region 54 decreases from w1 to w3 as shown. Exemplary values of the ratio of the width w with respect to the thickness t along the intermediate region 54 as a percentage of the distance from the optic periphery 50 to the bridge portion 64 are provided below in Table I.

TABLE I

| Percentage from optic to bridge portion (%) | Width w to thickness t ratio (range) |
| --- | --- |
| 20 | 12.95 (12:1–13:1) |
| 40 | 11.16 (10:1–12:1) |
| 60 | 9.37 (9:1–10:1) |
| 80 | 7.59 (8:1–9:1) |

Even at the radially outermost end of the intermediate region 54, as seen in FIG. 7C, the ratio of the width w3 with respect to the thickness t is at least about 2:1, and more preferably is at least about 3:1. In this manner, the intermediate region 54 possesses substantial stiffness in bending about either an axis that is parallel to the radial direction r (see FIG. 3), and about an axis (not shown) that is orthogonal to both the radial direction r and the axial direction Z. In other words, the intermediate region 54 provides substantial resistance to bowing or vaulting upon inward compression transmitted through the leg portions 66.

Furthermore, the relatively wide and stable intermediate region 54 facilitates folding and insertion of the IOL 40 within the small anterior chamber space. As mentioned, the IOL 40 is folded along an axis parallel to the fold line FL shown in FIG. 4. The wide intermediate regions 54 thus fold into tubular structures and the bridge portions 64 curl the leg portions 66 as well. The leg portions 66 do not extend substantially beyond the diameter of the optic 42, and thus the resulting folded IOL has no loose appendages. The folded IOL 40 can thus be controllably released and unfolded within the anterior chamber.

In an exemplary embodiment of the present IOL, diametrically-opposed foot members 68 are initially spaced apart across the optic 42 by a first distance, and flex inward so as to be spaced apart a second distance that is at least as large as the distance between bridge portions 64; the bridge portions 64 generally remaining the same distance apart. For example, the overall span (i.e., the first distance) across the diametrically-opposed foot members 68 in their relaxed state is between about 11–14 mm, while the distance between bridge portions 64 is between about 10–13 mm.

Another aspect of the invention is the advantageous shape and size of the foot members 68. As best seen in FIG. 5, the foot members 68 extend radially outward from the respective leg portion 66. In this regard, each leg portion 66 desirably has a rectangular or other shaped cross-section that is substantially constant between the bridge portion 64 and foot member 68. An inner wall 70 of each leg member 66 continues substantially without interruption to the end of the foot member 68. On the other hand, an outer wall 72 extends only to the foot member 68, which projects radially outward therefrom and has a generally rounded rectangular shape in plan view. This shape helps spread out the contact forces imparted to the surrounding tissue, thus reducing some of the problems associated with endothelial cell loss. Also, because of the continuous inner wall 70, contact between the leg member 66 and the intermediate region 54 (specifically the respective side edge 56 thereof) is avoided. That is, the potential angle of flexure of each leg member 66 is less than the angular space between the side edge 56 and inner wall 70.

While this invention has been described with respect to various specific examples and embodiments, it is to be understood that the invention is not limited thereto and that it can be variously practiced within the scope of the following claims. For example, although only two fixation members are shown, there may be three or more. Alternatively, any one of the disclosed fixation members may be used in combination with one or more other type of fixation member.

What is claimed is:

1. A foldable intraocular lens (IOL) for implantation in an anterior chamber of an eye, the IOL comprising:

an optic centered on an optical axis, the IOL defining a planar or domed surface that is substantially perpendicular with respect to the optical axis at least at its intersection with the optical axis; and at least one fixation member having a proximal end secured to the optic, an intermediate region extending generally radially outwardly from the proximal end and a distal region secured to an outer portion of the intermediate region, the intermediate region having a circumferential width (relative to the optical axis) that is at least twice as large as its axial thickness at all points, the distal region including at least one leg portion extending away from the outer portion of the intermediate region generally perpendicularly with respect to a radial line (relative to the optical axis) through the intermediate region, the leg portion able to flex in a direction parallel to the planar or domed surface of the IOL while the intermediate region being substantially unable to flex in a direction parallel to the planar or domed surface of the IOL.

2. The IOL of claim 1 including only two of the fixation members.

3. The IOL of claim 1 wherein the distal region includes two leg portions extending away from each other in substantially opposite directions.

4. The IOL of claim 3 wherein the two leg portions extend away from each other a distance equal to or less than a diameter of the optic to facilitate folding of the IOL.

5. The IOL of claim 4 wherein the leg portions each have an enlarged footplate on an outer end extending radially outwardly therefrom.

6. The IOL of claim 1 wherein the at least one leg portion is structured to flex as a result of a compressive fit within the eye on the at least one leg portion substantially without moving the optic parallel to the optical axis.

7. A foldable intraocular lens (IOL) for implantation in an anterior chamber of an eye, the IOL comprising:

an optic centered on an optical axis, the IOL defining a planar or domed surface that is substantially perpendicular with respect to the optical axis at least at its intersection with the optical axis; and at least one fixation member having a proximal end secured to the optic, an intermediate region extending generally radially outwardly from the proximal end, and a distal region secured to an outer portion of the intermediate region, the intermediate region having a circumferential width about the optical axis which is substantially smaller adjacent the outer portion than it is adjacent the proximal end, the distal region including at least one leg portion extending away from the outer portion of the intermediate region generally perpendicularly with respect to a radial line (relative to the optical axis) through the intermediate region, the leg portion being able to flex in a direction parallel to the planar or domed surface of the IOL while the intermediate region is substantially unable to flex in a direction parallel to the planar or domed surface of the IOL.

8. The IOL of claim 1 which is a single piece lens.

9. The IOL of claim 1 wherein the optic and the fixation members comprise one or more polymeric materials.

10. The IOL of claim 1 wherein the optic comprises a resiliently deformable polymeric material.

11. A foldable intraocular lens (IOL) for implantation in an anterior chamber of an eye, the IOL comprising:

an optic centered on an optical axis, the IOL defining a planar or domed surface that is substantially perpendicular with respect to the optical axis at least at its intersection with the optical axis; and at least one fixation member exhibiting an angular transition so as to be stepped from the plane of the IOL, the fixation member having a proximal end secured to the optic, an intermediate region extending generally radially outwardly from the proximal end, and a distal region secured to an outer portion of the intermediate region, the distal region including at least one leg portion extending away from the outer portion of the intermediate region generally perpendicularly with respect to a radial line (relative to the optical axis) through the intermediate region, the leg portion being able to flex in a direction parallel to the planar or domed surface of the IOL while the intermediate region is substantially unable to flex in a direction parallel to the planar or domed surface of the IOL.

12. A foldable intraocular lens (IOL) having reduced optic vaulting for implantation in an anterior chamber of an eye, the IOL comprising:

an optic centered on an optical axis, the IOL defining a planar or domed surface that is substantially perpendicular with respect to the optical axis at least at its intersection with the optical axis; and at least one fixation member having a proximal end secured to the optic, an intermediate region extending generally radially outwardly from the proximal end and a distal region secured to an outer portion of the intermediate region, the distal region being able to flex in a direction parallel to the planar or domed surface of the IOL, and the intermediate region having a circumferential width about the optical axis which is substantially smaller adjacent the outer portion than it is adjacent the proximal end.

13. The IOL of claim 12 the distal region including at least one leg portion extending away from the outer portion of the intermediate region generally perpendicularly with respect to a radial line (relative to the optical axis) through the intermediate region, the leg portion being configured to radially flex in a direction parallel to the planar or domed surface of the IOL.

14. The IOL of claim 13 wherein the distal region includes two leg portions extending away from each other in substantially opposite directions.

15. The IOL of claim 14 wherein the two leg portions extend away from each other a distance equal to or less than a diameter of the optic to facilitate folding of the IOL.

16. The IOL of claim 13 wherein the leg portion has an enlarged footplate on an outer end extending radially outwardly therefrom.

17. The IOL of claim 12 wherein the intermediate region has a circumferential width (relative to the optical axis) that is at least twice as large as its axial thickness at all points.

18. The IOL of claim 17 wherein the intermediate region has a diverging circumferential width from the outer portion to the proximal end thereof.

19. A foldable intraocular lens (IOL) for implantation in an anterior chamber of an eye, the IOL comprising:

an optic centered on an optical axis, the IOL defining a planar or domed surface that is substantially perpendicular with respect to the optical axis at least at its intersection with the optical axis; and at least one fixation member having a proximal end secured to the optic, an intermediate region extending generally radially outwardly from the proximal end, and a distal region secured to an outer portion of the intermediate region, the distal region including two leg portions extending away from the outer portion of the intermediate region generally perpendicularly with respect to a radial line (relative to the optical axis) through the intermediate region and away from each other in substantially opposite directions, wherein the two leg portions extend away from each other a distance equal to or less than a diameter of the optic to facilitate folding of the IOL.

20. A foldable intraocular lens (IOL) for implantation in an anterior chamber of an eye, the IOL comprising:

an optic centered on an optical axis and having a peripheral edge, the IOL defining a planar or domed surface that is substantially perpendicular with respect to the optical axis at least at its intersection with the optical axis; and at least one fixation member for supporting the optic in the anterior chamber, the fixation member including an intermediate region having a length extending from the peripheral edge of the optic to an outer edge and having uniform axial thickness throughout the length, and at least one leg portion joined to the intermediate region at the outer edge and extending generally perpendicularly with respect to a radial line (relative to the optical axis) through the intermediate region, the leg portion being structured to flex in a direction parallel to the planar or domed surface of the IOL while the intermediate region is structured to be substantially unable to flex in a direction parallel to the planar or domed surface of the IOL.

* * * * *